(12) United States Patent
Dong et al.

(10) Patent No.: US 7,578,851 B2
(45) Date of Patent: Aug. 25, 2009

(54) GRADIENT POROUS IMPLANT

(75) Inventors: Nicholas Nai Guang Dong, Little Falls, NJ (US); Aiguo Wang, Wayne, NJ (US); Eric Jones, Limerick (IE); Gregory E. Plaskon, Clifton, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 193 days.

(21) Appl. No.: 11/317,229

(22) Filed: Dec. 23, 2005

(65) Prior Publication Data

US 2007/0150068 A1 Jun. 28, 2007

(51) Int. Cl.
*A61F 2/32* (2006.01)

(52) U.S. Cl. .................................... 623/22.21
(58) Field of Classification Search ............. 623/23.5, 623/23.55, 22.21, 22.33, 22.32, 22.22, 22.29, 623/22.39, 22.43, 23.56, 22.23
See application file for complete search history.

(56) References Cited

U.S. PATENT DOCUMENTS

| | | | |
|---|---|---|---|
| 4,536,894 A | 8/1985 | Galante et al. | |
| 4,542,539 A * | 9/1985 | Rowe et al. | 623/23.57 |
| 4,778,474 A | 10/1988 | Homsy | |
| 5,658,345 A * | 8/1997 | Willi | 623/22.26 |
| 6,136,033 A | 10/2000 | Suemer | |
| 6,277,150 B1 | 8/2001 | Crawley et al. | |
| 6,290,726 B1 | 9/2001 | Pope et al. | |
| 6,319,285 B1 | 11/2001 | Chamier et al. | |
| 6,352,559 B1 | 3/2002 | Church | |
| 6,475,243 B1 | 11/2002 | Sheldon et al. | |
| 6,488,715 B1 | 12/2002 | Pope et al. | |
| 6,494,916 B1 | 12/2002 | Babalola et al. | |
| 6,514,288 B2 | 2/2003 | Meulink et al. | |
| 6,517,583 B1 | 2/2003 | Pope et al. | |
| 6,520,995 B2 | 2/2003 | Church | |
| 6,652,590 B1 | 11/2003 | Zitnansky et al. | |
| 6,673,108 B2 | 1/2004 | Zilla et al. | |
| 6,709,462 B2 * | 3/2004 | Hanssen | 623/22.35 |
| 6,712,857 B1 | 3/2004 | Roger | |
| 6,758,864 B2 | 7/2004 | Storer et al. | |
| 6,793,681 B1 | 9/2004 | Pope et al. | |
| 2002/0107577 A1 | 8/2002 | Storer et al. | |
| 2002/0120344 A1 | 8/2002 | Meulink et al. | |
| 2003/0045941 A1 | 3/2003 | Lewallen | |

(Continued)

*Primary Examiner*—Corrine M McDermott
*Assistant Examiner*—Christopher D Prone
(74) *Attorney, Agent, or Firm*—Lerner, David, Littenberg, Krumholz & Mentlik, LLP

(57) ABSTRACT

An implantable medical device includes a porous metal foam or foam-like structure having pores defined by metal struts or webs wherein the porous structure has directionally controlled pore characteristics. The pore characteristics controlled include one or more of the metal structure porosity, pore size, pore shape, pore size distribution and strut thickness. The pore characteristics may vary in one or more directions throughout the structure. Preferably the pore characteristics are controlled to match the porous metal structure to various mechanical and biological requirements of different regions of the structure in order to optimize aspects of the implants performance and may vary not only over the surface of the porous structure but through the depth of the porous structure. The thickness of the porous metal structure may also be modified to establish a thickness profile that optimizes mechanical and biological requirements of the implants performance. Acetabular cup embodiments of the invention are described. Various methods of manufacturing implants having directionally controlled pore characteristics are described.

32 Claims, 11 Drawing Sheets

U.S. PATENT DOCUMENTS

| | | |
|---|---|---|
| 2003/0074079 A1 | 4/2003 | McTighe et al. |
| 2003/0153981 A1* | 8/2003 | Wang et al. .............. 623/22.21 |
| 2004/0122524 A1 | 6/2004 | Hunter et al. |
| 2004/0225369 A1 | 11/2004 | Lakin et al. |
| 2004/0225370 A1 | 11/2004 | Cruchet et al. |
| 2004/0243237 A1* | 12/2004 | Unwin et al. ............ 623/17.11 |
| 2004/0243247 A1 | 12/2004 | Kuoni et al. |
| 2005/0070989 A1 | 3/2005 | Lye et al. |

* cited by examiner

A-A

B-B

GRADIENT POROUS IMPLANT

BACKGROUND OF THE INVENTION

The present invention relates to implantable medical devices, and in particular to metallic porous structures for implantable medical devices including orthopedic implants, especially acetabular cup implants, methods of forming such metallic porous layers for implants, and methods of producing such devices.

The use of orthopedic implants is the result of deterioration of human bone structure, usually because of various degenerative diseases, such as osteoarthritis. In recent years, a variety of implantable orthopedic devices have been developed. Typically, the failed bone structure is replaced with an orthopedic implant that mimics, as closely as possible, the structure of the natural bone and performs its functions.

Orthopedic implants are constructed from materials that are stable in biological environments and withstand physical stress with minimal or controlled deformation. Such materials must possess strength, resistance to corrosion, biocompatibility, and good wear properties. Also, the implants include various interacting parts, which undergo repeated long-term physical stress inside the body.

A breakdown of a permanently installed implant leads to pain, limitation on the range of motion, and may require a replacement of the implant. For these reasons, among others, the bone/implant interface and the connection between various parts of the implant must be resistant to breakdown. It is especially important since installation of an orthopedic implant often involves an extensive and difficult medical procedure, and therefore replacement of the installed implant is highly undesirable.

The requirements for the useful life of the implant continue to grow with the increase in human life expectancy. The strength and longevity of implants in large part depend on the bone/implant interface. Various methods of connection are known in the art. For example, a hip joint is a ball-in-socket joint, and includes a rounded femoral head and a cup-like socket (acetabular cup) located in the pelvis. The surfaces of the rounded femoral head and the acetabular cup continually abrade each other as a person walks. The abrasion, along with normal loading, creates stress on the hip joint and adjacent bones. If the femoral head or the acetabular cup is replaced with an implant, this stress must be well tolerated by the implant's bearing surfaces to prevent implant failure.

FIG. 1 shows a typical hip replacement system that includes an acetabular cup prosthetic implant assembly 10 and a femoral prosthesis 20. Generally, the acetabular cup implant 10 includes a bone interface shell 11 and a socket bearing insert 12. The femoral prosthesis 20 includes a femoral stem 21 and a femoral head in the form of a ball 22, which moves inside the socket insert 12 of the acetabular cup implant 10. The femoral ball 22 usually has a polished surface to maintain a low friction interface with the surface of the socket insert 12 of the acetabular cup implant 10. The stem section 26 is inserted into the interior of the femur.

The socket insert 12 is usually made from a plastic material such as polyethylene or ultra high molecular weight polyethylene (UHMWPE), but may be of any biocompatible bearing material that has sufficient strength and wear resistance to withstand the loading and the abrasive nature of the joint. The socket insert 12 is typically held in the shell 11 by a series of locking grooves or notches. Ceramics and metals are also used to make socket insert 12 and in some instances the socket insert 12 is integral with the bone interface shell 11 so that the interior surface of the shell 11 acts as the bearing. The shell 11 is typically made from a metal such as titanium or cobalt-chrome alloy, and has a bone interface surface 16.

In use, the complete acetabular cup implant 10 may be attached to the patient's pelvis by a series of locking grooves, pins or screws 29, usually in conjunction with bone cement. Alternatively, the acetabular cup implant 10 may be press-fit by being driven into the patient's acetabulum with an impaction tool in situations where patient-related criteria are met. Press fit cementless acetabular cups have become the gold standard for an acetabular bearing component due to the favorable clinical results and surgical advantages. The most desirable cementless acetabular cup is a cup with a three dimensional bony in-growth microstructure surface, such as a porous surface layer. This method avoids the use of bone cement. The bone ingrowth into the voids of the porous bone interface layer provides skeletal fixation for the implants used for replacement of bone segments. In addition to providing a strong fixation, the bone ingrowth improves biocompatibility of the implant and is even believed by some to promote positive biochemical changes in the diseased bone. To implement this approach, it is important to develop improved methods of constructing porous outer layers on the bone interface surfaces of implants.

Depending on the type of bone, the location of the bone within the body, individual characteristics and disease state, bone has a wide variation in mechanical characteristics. Bone is generally categorized as trabecular or cancellous bone, which is porous and has an open cancellated structure, and cortical bone, which is dense. Subchondral bone, as found in the acetabulum, is also dense. It should be noted that the mechanical property values for trabecular and cortical bone overlap and often form a continuum within a given bone of the body. Wide ranges of mechanical properties for bone are reported in the literature, even for bone of the same type. Typically, trabecular bone has a tensile strength of 8 MPA as a mid range value. Cortical bone has a tensile strength approximately 15 times higher, 120 MPA as a mid range value. For comparison, the common implant metal titanium Ti6-Al4-V alloy, in solid form, has a tensile strength of 965 MPA. Cortical bone has a modulus of elasticity on the order of 30 times higher than the apparent modulus of elasticity of trabecular bone.

Orthopedic implants with porous bone interface surfaces have been studied extensively over the last twenty years. In view of the strength and longevity requirements, the implants are typically made of biocompatible metals, such as titanium or cobalt-chrome alloy. It has long been known that success in facilitating the ingrowth is related to the pore characteristics of the bone interface surfaces, such as pore size, pore topography and porosity. For example, it is known that the bone ingrowth may be almost entirely non-existent if the porous layer has pore sizes of less than 10 μm, and that pore sizes greater that 100 μm facilitate the ingrowth. For further example, it is known that the pores must interconnect to allow sufficient depth of bone ingrowth and flow of biological fluids.

Thus, one of the challenges is to provide metallic orthopedic implants having porous metallic bone interfaces with appropriate pore sizes, high pore connectivity and high porosity. Another challenge is to provide appropriate matching of mechanical properties between the porous layer and the underlying solid substrate, such as the inner solid portion of the shell 14 and the porous portions of the shell 11, respectively, of the acetabular cup implant 10 shown in FIG. 1. Likewise, it is desirable to match the properties of the porous outer portion of the shell 13 with the characteristics of the bone, which change over the surface of the implant. For example, the equatorial rim 17 of the acetabular cup implant 10 contacts dense bone in the corresponding region of the acetabulum while the dome region near the pole 18 contacts more porous cancellous or less dense subchondral bone in the corresponding region of the acetabulum. Additionally, it is desirable to match the mechanical properties of the implant to the bone in order to minimize the differences in the strain field at the interface to avoid loosening the bone/implant bonds and to properly distribute loading over the bone so as to avoid stress shielding and consequent resorption of bone. This requires matching the modulus of elasticity of the outer layer of the porous metal coating with the bone modulus of elasticity over any portion of the bone/implant interface subject to load. On a macro level, it is further desirable to match the overall resilience of the dome region of the acetabular cup implant to the resilience of the acetabulum to provide a more natural dynamic load path into the pelvis and better absorb impacts on the joint.

An additional challenge is that implants with an open porous structure are generally mechanically weaker than those with a denser, less porous, structure. It is desirable to improve the integrity of porous structures in highly stressed regions during installation and during use, both from a mechanical and a biological perspective.

Considering the conflicting requirements for optimizing tissue ingrowth, substrate compatibility, bone compatibility and mechanical considerations for the porous bone interface surfaces particular to a given implant, there is a need for implant designs and manufacturing methods that better meet these conflicting requirements.

Certain orthopedic implants having porous bone interface surfaces, and related methods of making such implants have been patented. Porous surfaces created by plasma spraying, flame spraying or sintering of metal particles such as spheres or wires onto the implant substrate are well known in the art. Such methods do not provide a high porosity (typically they are below 50%), high cell interconnectivity or optimum control of pore characteristics. For example, U.S. Pat. No. 5,926,685 describes a method of forming an implant having a porous outer surface by using an organic binder compound to enhance the binding between the porous surface layer and the implant. The binder and metal particles that form the porous layer are mixed and the mixture is placed in contact with a solid surface of the metallic implant. Then, the particles (precursor of the porous layer) are bound to each other and to the solid surface of the implant via a sintering process.

In general, methods of producing high porosity metallic structures with controlled pore characteristics are known in the art. As shown in FIG. 2, such structures are typically cancellated space frame structures with struts or webs 32 defining somewhat regular shaped pores 34 and have high interconnectivity and relatively uniform pore characteristics. Typically this type of structure is formed based on the shape of a polymer foam precursor, either used as a skeleton for metallic coating or used to create a mold for a casting. The porosity of such structures is typically 60%-90% or even higher. This type of structure is very similar to that of cancellous bone, where the bone trabeculae form the struts. Furthermore, such a cancellated space frame structure is highly interconnected, allowing, in the case of a structure suitable for an implant, bone growth, vascularization and fluid flow throughout the interconnected pores.

U.S. Pat. No. 5,282,861 describes such an open cell structure for bone implants having pore volume of from 70 to 80%. The open cell structures of the '861 patent are formed by chemical vapor deposition of tantalum on a carbon skeleton to form a carbon-tantalum composite. The resulting structures have a carbon core and a tantalum outer surface. The specification of the '861 patent emphasizes that the three-dimensional porosity of this structure is uniform and consistent.

U.S. Pat. No. 5,976,454 describes a process for producing nickel foam for use in making battery electrodes. The porosity of the foam is over 90%, but it is produced by a method that is in many respects not suitable for producing foams of biocompatible metals typically used in making implants, such as tantalum or titanium.

In order to partially address the conflicting requirements for optimizing tissue ingrowth, substrate compatibility, bone compatibility and mechanical considerations for the porous bone interface surfaces particular to a given implant, several patents have proposed limited variations in the directional pore characteristics of the bone interface surfaces. U.S. Pat. No. 4,542,539 describes an implant with multiple layers of particles deposited on the surface. As shown in FIG. 3, the particles 42 increase in size from the substrate 44 of the implant to the bone interface surface 46 in the direction normal to the substrate as shown in FIG. 3. Purportedly, variation in the angle of incidence of the particles in the layer by layer deposition of the particles by a flame-plasma process results in a larger pore size and porosity at the surface. The porosity and interconnectedness is not said to be directly controllable. Because the particles occupy the bulk of the volume, this type of porous structure cannot approach the porosity, interconnectivity and mechanical integrity of a cancellated structure. The reference distinguishes variation of the pore sizes in the direction normal to the substrate from other references that have different pore sizes on different parts of the surface such as U.S. Pat. No. 5,489,306 discussed below.

U.S. Patent Application No. 2005/0100578 describes a method of achieving a porosity gradient in a porous implant through the thickness of a material by stacking layers of porous sheets and bonding the sheets together. Purportedly, the sheets can be fabricated so that features align from sheet to sheet to create a controlled porosity gradient in the direction normal to stacking.

U.S. Pat. No. 5,489,306 describes an implant with graduated size particles in different zones of the surface from the proximal to distal end of the implant to create different pore sizes on different zones of the surface. Each zone only has pores within a designated, relatively narrow, range, with the goal of encouraging a specific extent and type of osteointegration in each zone. No variation in the pore size in the direction normal to the substrate is disclosed and there is no discussion of the variation of other pore characteristics such as the porosity.

U.S. Pat. No. 6,913,623 describes an implant with a metal core and a proximal body fused to the core having a lower modulus of elasticity and a higher porosity than the core. The porosity of the proximal body may be variable or functionally gradient throughout. There is no disclosure of how the porosity varies or how the variation is to be achieved.

U.S. Pat. No. 5,986,169 describes implants formed from Nickel-titanium alloys that are made porous by a combustion synthesis method developed in Russia. While claiming to produce a controlled porosity and porosity distributions, the porosity distributions described are broader than those described in other references for optimization of a porous implant. No description of gradient porosities or how to achieve a gradient porosity is provided.

U.S. Patent Application No. 2003/0074081 purports to describe a method of producing implants having a controlled and directional gradient of porosity through all or one or more portions of an implant. Allusions are made to combustion synthesis methods generally as providing the method of creating a graded porosity. The only related example provided in the application describes the Nickel-Titanium combustion synthesis method developed in Russia that is the topic of U.S. Pat. No. 5,986,169 described above. The example provided does not disclose a method for creating a gradient porosity implant.

Various patents describe acetabular cups with resilient and relatively flexible dome regions for the purposes of reducing impacts to the bearing surfaces and the implant/bone interfaces. This has the advantages of potentially increasing the bearing life, preserving the fixation of the cup, and increasing the comfort of implant to the user. Examples include U.S. Pat. No. 6,136,033, and United Kingdom Patents 2,126,096, 1,189,325 and 1,527,498. These devices allow relative movement of the bearing surface with respect to the cup outer surface contacting the bone by allowing the outer surface to freely flex or by interposing an elastomeric material between the bearing surface and the outer surface. There is a need to provide increased resilience and decreased rigidity of the dome region of an acetabular cup without the additional cup thickness, machining and components required for these methods.

It is also desirable to create an acetabular cup with a relatively more rigid rim region of the cup. Because the cup is initially an interference fit in the acetabular socket, the cup may have large radial loads in the rim region once installed that can distort the hemisphere in that region inward and create excess bearing stress and even binding in the equatorial region of the bearing surface. This problem can be particularly aggravated by an under-reamed acetabular socket.

Therefore, there exists a continuing need for implantable medical devices, especially orthopedic implants, having metallic porous surfaces, blocks, layers or other porous structures for interfacing with bones and/or other tissue, with the porous structures having a variety of directionally controlled pore characteristics, including controlled porosity, controlled pore size and controlled pore size distribution, and with the porous structures having such controlled pore characteristics, strength, elasticity and configurations to optimize the performance of implantable medical devices.

SUMMARY OF THE INVENTION

Various aspects of the present invention address this need.

Thus, in accordance with one aspect, the invention provides an implantable medical device comprising a porous metal foam or foam-like structure having pores defined by metal struts or webs wherein the porous structures have directionally controlled pore characteristics. The pore characteristics controlled include one or more of the metal foam porosity, pore size, pore shape, pore size distribution and strut thickness. The pore characteristics may vary in one or more directions throughout the structure.

Preferably the pore characteristics are controlled to match the porous metal foam structure to various mechanical and biological requirements of different regions of the structure in order to optimize various aspects of the implants performance. The requirements include matching the bone characteristics adjacent the structure, such as the bone porosity, strength and modulus of elasticity. Other requirements include matching the characteristics of the substrate of the implant to which the porous metal foam structure is attached, such as the substrate strength and modulus of elasticity. Thus the pore characteristics vary not only over the surfaces of the porous layer, but through the depth of the porous layer depending on the matching requirements of the particular implant.

In another aspect, the invention modifies the thickness of the porous metal foam or foam-like structure in different regions of the structure in order to establish a thickness profile that optimizes various mechanical and biological requirements of the implants performance. These requirements include increasing the thickness of the structure adjacent cancellous bone to allow deeper bone ingrowth in the higher growth cancellous bone region and to allow the implant to be less rigid and more resilient in order to better match the cancellous bone characteristics, and if desired, better transmit the joint load against the bone. Conversely, the thickness of the porous structure is decreased or the thickness of the solid structure is increased adjacent peripheral denser bone in response to typically higher insertion loads imposed in the region. This increase in rigidity around the rim maximizes the cups dimensional stability which is required for certain hard on hard bearings.

In another aspect, the invention is an acetabular cup implant with an outer, generally hemispherical, porous metal foam or foam-like layer for contacting bone. The outer layer has a first porosity and thickness in the equatorial or rim region that is typically in contact with dense bone of the acetabulum and a second porosity and thickness in the polar or dome region that is generally in contact with the cancellous bone of the acetabulum. The second thickness is greater than the first thickness to allow deeper bone ingrowth and to allow the dome to be less rigid and more resilient in order to better match the cancellous bone characteristics. If the dome region is more porous or has other pore characteristics that decrease the modulus of elasticity in the dome region, such as thinner struts in the cancellated structure, this further augments the desired decrease in rigidity and increase in resiliency of the dome region.

In accordance with an aspect, the invention is an acetabular cup implant with an outer, generally hemispherical, porous metal foam or foam-like layer for contacting bone. The outer layer surface has a first porosity gradient in the equatorial or rim region and a first surface porosity in the equatorial or rim region that is typically in contact with denser bone of the acetabulum. The outer surface layer also has a second porosity gradient in the polar or dome region and a second surface porosity in the polar or dome region that is generally in contact with the cancellous or less dense subchondral bone of the acetabulum. The second surface porosity is greater than the first surface porosity to better allow cancellous bone ingrowth and to allow the dome to be less rigid and more resilient in order to better match the cancellous bone characteristics. The porosity in each region decreases with depth from each respective surface porosity to a lower porosity that better matches the strength and modulus of elasticity of the shell substrate.

It will be understood by a person of skill in the art that throughout this specification when first and second regions or zones, first and second porosity gradients and first and second surface porosities have been described, these zones, porosity gradients and surface porosities may be adjusted and varied to provide gradients of porosity in three dimensions throughout the volume of the porous metal layers and that additional discrete intermediate zones, porosity gradients and surface porosities may also be defined, adjusted and varied to transition between the first and second regions, first and second porosity gradients and first and second surface porosities described above to provide varying porosities and porosity gradients in different regions throughout the volume of the generally hemispherical porous metal layer. Furthermore it will be understood that that where gradients are described, they may consist of stepwise transitions rather than continuous smooth transitions. One particular reason for such stepwise transitions is because the pores sizes are discrete increments of space. For example, a thin porous layer may be only two pore size units thick and thus a gradient of pore size through such a layer must be a step in size. Gradients that have stepwise transitions may also result from particular manufacturing methods.

In accordance with another aspect, the invention provides a method of forming a gradient porous metal foam structure for use in an implantable medical device based on the methods described in U.S. patent application Ser. No. 10/071,667 filed on Feb. 8, 2002 and published as U.S. Published Patent Application 20030153981 herein incorporated by reference. In one aspect, the invention of the '981 application provides a porous metal scaffold comprising a porous metal network having pores defined by metal webs or struts, the metal webs covered with at least one layer of metal particles bonded to the metal webs. In other aspects, the invention provides methods of forming porous scaffolds. In one such aspect, the method includes providing a polymer foam preform; forming a skin of biocompatible metal on the polymer foam preform by low temperature arc vapor deposition; and heating the polymer foam and the metal skin above the decomposition temperature of the polymer foam preform in an inert gas atmosphere; thereby the polymer foam preform decomposes producing a green metal foam. The methods of the '981 application are extended in the present invention to the fabrication of gradient and zonal porous scaffolds or foam structures for implants by new methods that provide varying porosities and porosity gradients in different regions throughout the volume of the porous metal foam layer of the implant.

In one aspect of the invention, the polymer foam preform is modified to have gradient pore characteristics corresponding to the desired gradient or zonal porosity or other pore characteristics of the finished implant, with a suitable allowance for the thickening of the webs by the subsequent metal deposition. Such a gradient porosity polymer may be created, for example, by the natural buoyancy of the gases in the liquid polymer foam, centrifuging of the liquid foam prior to setting, selected permanent compression of a constant porosity polymer foam precursor to form the gradient porosity preform or by rapid prototyping techniques.

In accordance with this aspect, the invention provides a method of forming a gradient porous metal foam structure for use in an implantable medical device, the method including:

providing a polymer foam preform having a pre-determined thickness profile and predetermined gradient pore characteristics;

forming a skin of biocompatible metal on the polymer foam perform by low temperature arc vapor deposition;

heating the polymer foam and the metal skin above the decomposition temperature of the polymer foam in an inert gas atmosphere; thereby the polymer foam decomposes producing a green metal foam having gradient pore characteristics.

Preferably, the method of this aspect of the invention further includes thickening the green metal foam by applying a solution of a binder onto the green foam, applying a metal powder having a pre-determined particle size, and sintering the foam, thus producing a final metal foam having gradient or zonal pre-determined pore characteristics. The thickening of the foam may be repeated until the metal foam has the final pre-determined pore characteristics.

In another aspect of the invention, the low temperature arc vapor deposition process described in the '981 application, or other physical deposition processes, are modified to utilize the directionality of the vapor flux deposited onto the polymer foam in order to build the metal skin to various thicknesses in different regions of the foam and thereby vary the pore characteristics, such as the porosity. Low pressure physical vapor deposition processes tend to produce line of sight coating patterns that build up more heavily on the side of the foam facing the vapor source as opposed to surfaces oblique to the source, facing away from the source or in a "shadow" created by overlying foam or other overlying objects. Such shadows may also be artificially created by the use of masks placed between the vapor source and the foam to allow less vapor deposition on selected regions of the implant.

In accordance with this aspect, the invention provides a method of forming a gradient porous or zonal metal foam structure for use in an implantable medical device, the method including:

providing a polymer foam having a pre-determined thickness profile and predetermined pore characteristics;

forming a skin of biocompatible metal having a gradient of skin thickness on the polymer foam by low temperature physical vapor deposition;

heating the polymer foam and the metal skin above the decomposition temperature of the polymer foam in an inert gas atmosphere; thereby the polymer foam decomposes producing a green metal foam having gradient pore characteristics.

Preferably, the method of this aspect of the invention further includes thickening the green metal foam by applying a solution of a binder onto the green foam, applying a metal powder having a pre-determined particle size, and sintering the foam, thus producing a final metal foam having gradient or zonal pre-determined pore characteristics. The thickening of the foam may be repeated until the metal foam has the final pre-determined pore characteristics.

In another aspect of the invention, the process of thickening the green metal foam by applying a solution of a binder onto the green foam, applying a metal powder having a pre-determined particle size, and sintering the foam described in the '981 application, is modified to selectively sinter varying amounts of metal powder to different regions of the green metal foam to vary the pore characteristics, such as porosity. Variations in the amount of metal powder sintered to the foam can be created by varying the amount and location of binder applied, varying the amount and location of metal powder applied, and by selectively removing binder or metal powder prior to sintering. As described in the '981 application, the cycle of applying the binder, applying the metal powder and sintering can be repeated. By applying and sintering the metal powder to selected regions during latter cycles, the porosity, for instance, can be reduced in the selected regions.

In accordance with this aspect, the invention provides a method of forming a gradient or zonal porous metal foam structure for use in an implantable medical device, the method including:

providing a polymer foam having a pre-determined thickness profile and predetermined pore characteristics;

forming a skin of biocompatible metal on the polymer foam by low temperature physical vapor deposition;

heating the polymer foam and the metal skin above the decomposition temperature of the polymer foam in an inert gas atmosphere; thereby the polymer foam decomposes producing a green metal foam having gradient pore characteristics.

The method of this aspect of the invention further includes variably thickening the green metal foam by applying a solution of a binder onto the green foam, applying a metal powder having a pre-determined particle size, and sintering the foam, thus producing a final metal foam having gradient pre-determined pore characteristics. The variable thickening of the foam may be repeated until the final metal foam has the pre-determined pore characteristics.

In accordance with another aspect, the invention provides a method of forming a gradient porous metal foam structure for use in an implantable medical device using laser sintering methods such as the methods described in commonly assigned U.S. patent application Ser. No. 10/704,270 filed on Nov. 7, 2003, titled "Laser-Produced Porous Surface", and published as U.S. Published Patent Application US 20040191106, herein incorporated by reference herein and the methods described in U.S. patent application Ser. No. 11/027,421 filed on Dec. 30, 2004, "Laser-Produced Porous Structure", incorporated by reference herein. The inventions of these applications provide a porous or partially porous three-dimensional metal article for use as a tissue ingrowth surface on a prosthesis. The porous article is formed using direct laser remelting in a cross section of a layer of metallic powder. The power, speed, spot size and beam overlap of the scanning laser is coordinated so that a predetermined porosity of the metallic powder can be achieved for each layer. Laser factors also vary depending on the thickness of the powder layer, type of metallic powder and size and size distribution of the powder particles. Successive depositing and remelting of individual layers are repeated until the article is fully formed in a layer-by-layer fashion. As explained in the applications the length and thickness of struts, the shape of unit cells (and consequently pores) and the overlapping of cells allow adjustment of the porosity throughout the structure. The pore characteristics can be varied from one location on the structure to another and the porosity of successive layers can be varied by these and other techniques described in the application. The methods can create a structure with an integral solid layer, or the porous layer can be formed on a pre-existing solid substrate, or the substrate can be attached to the porous structure by methods such as conventional sintering. Thus a laser sintering approach can also be used to fabricate the various aspects of the invention described above.

Figure 4:
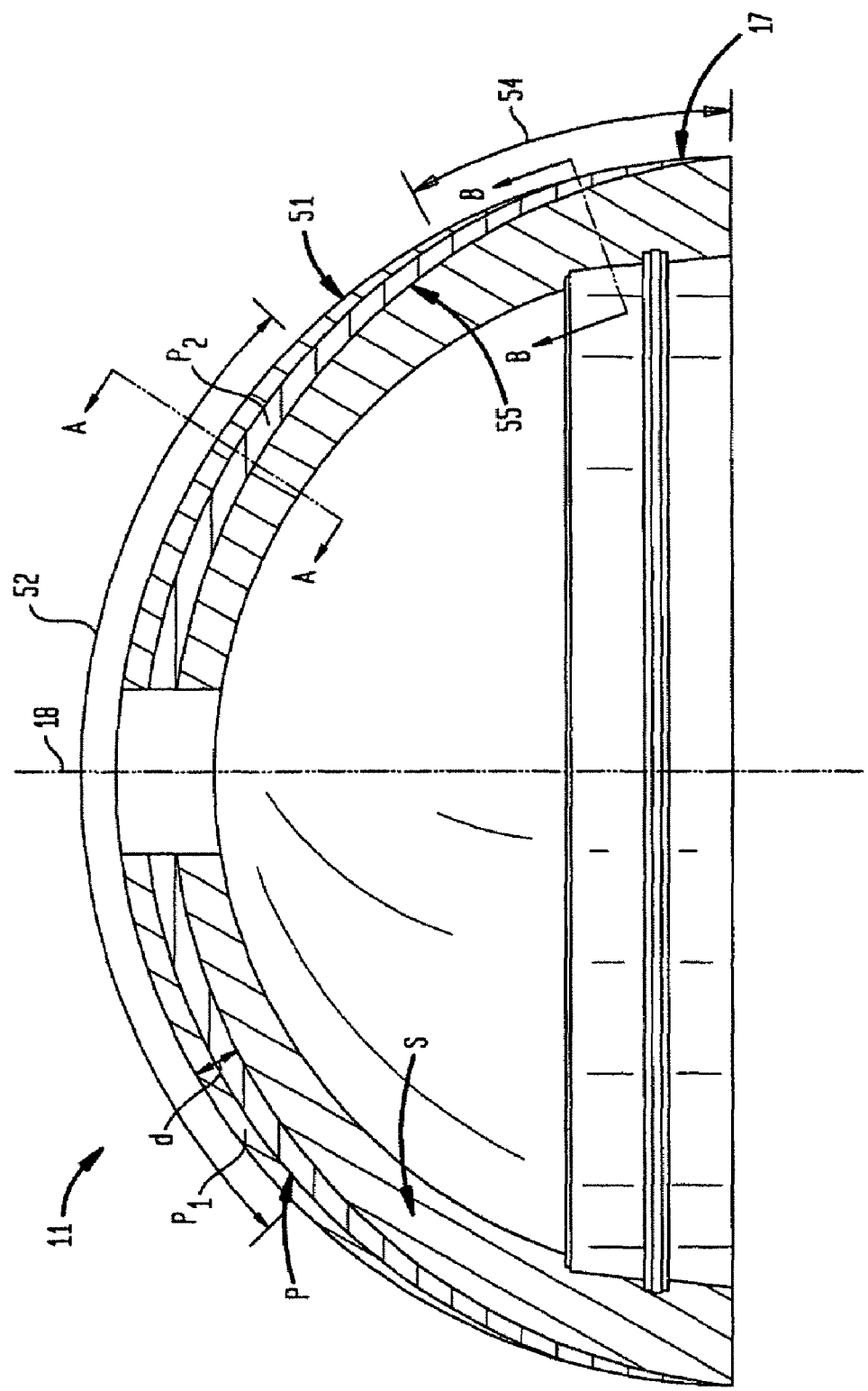
Figure 5:
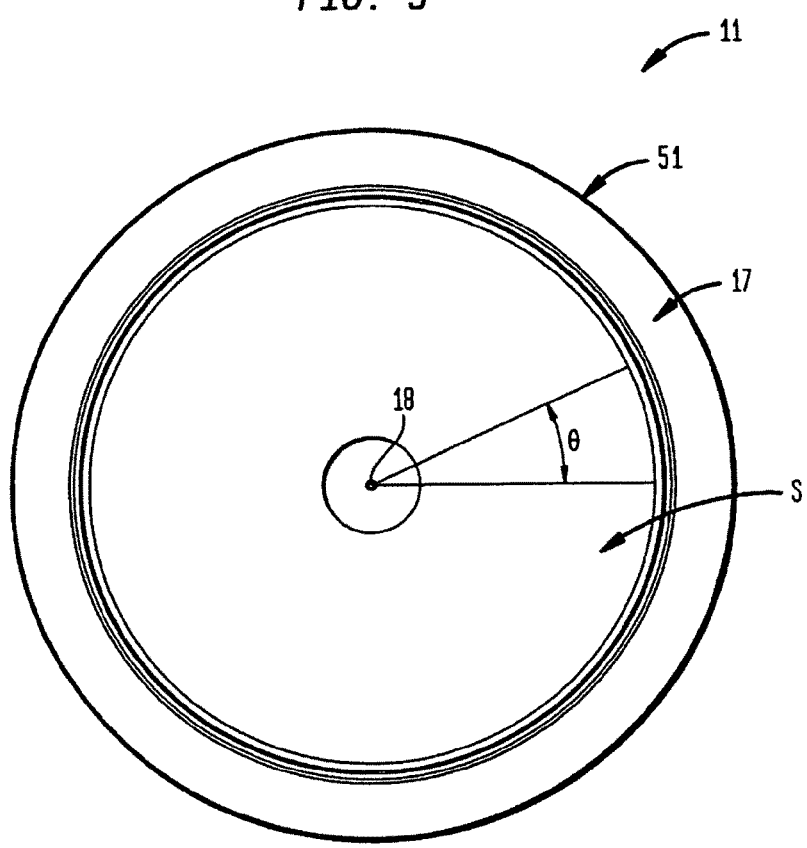
Figure 6:
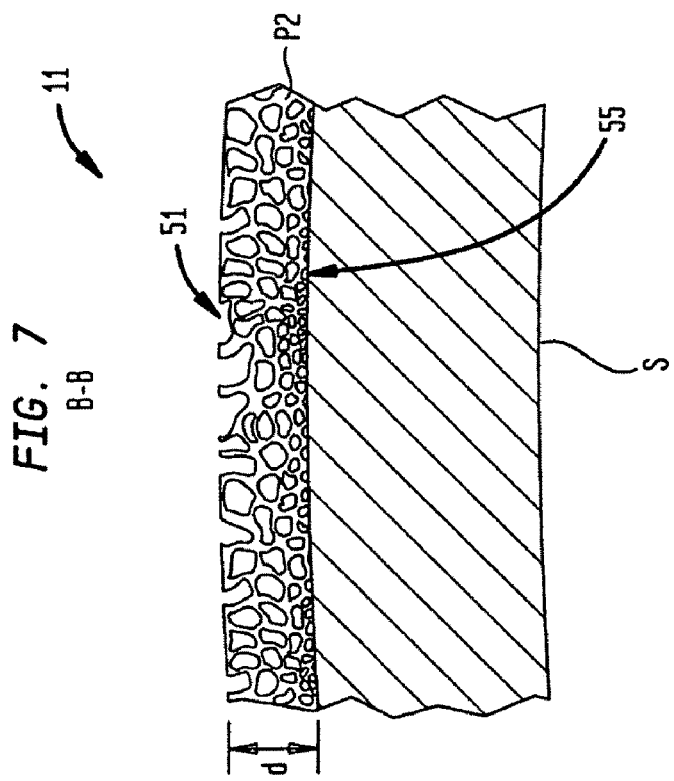
Figure 7:
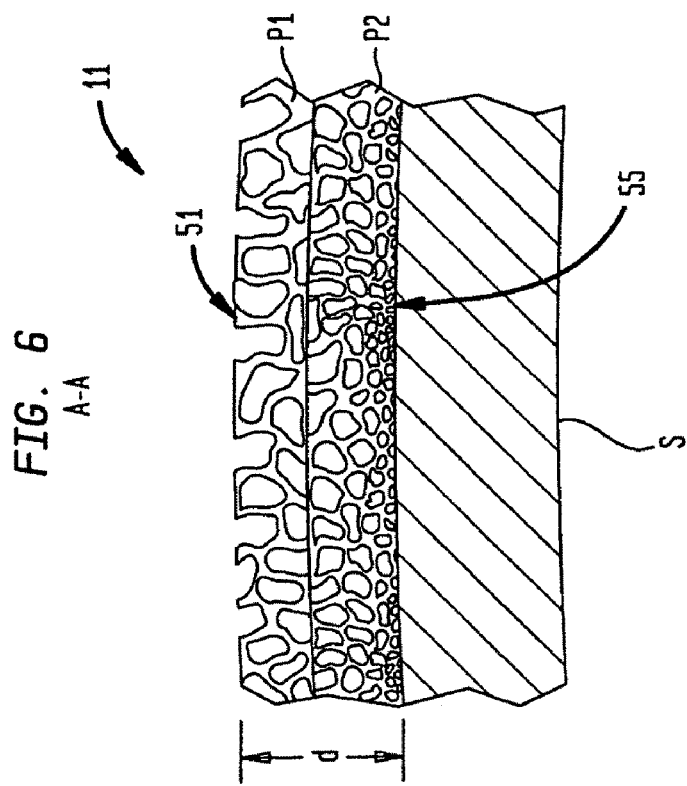
Figure 8:
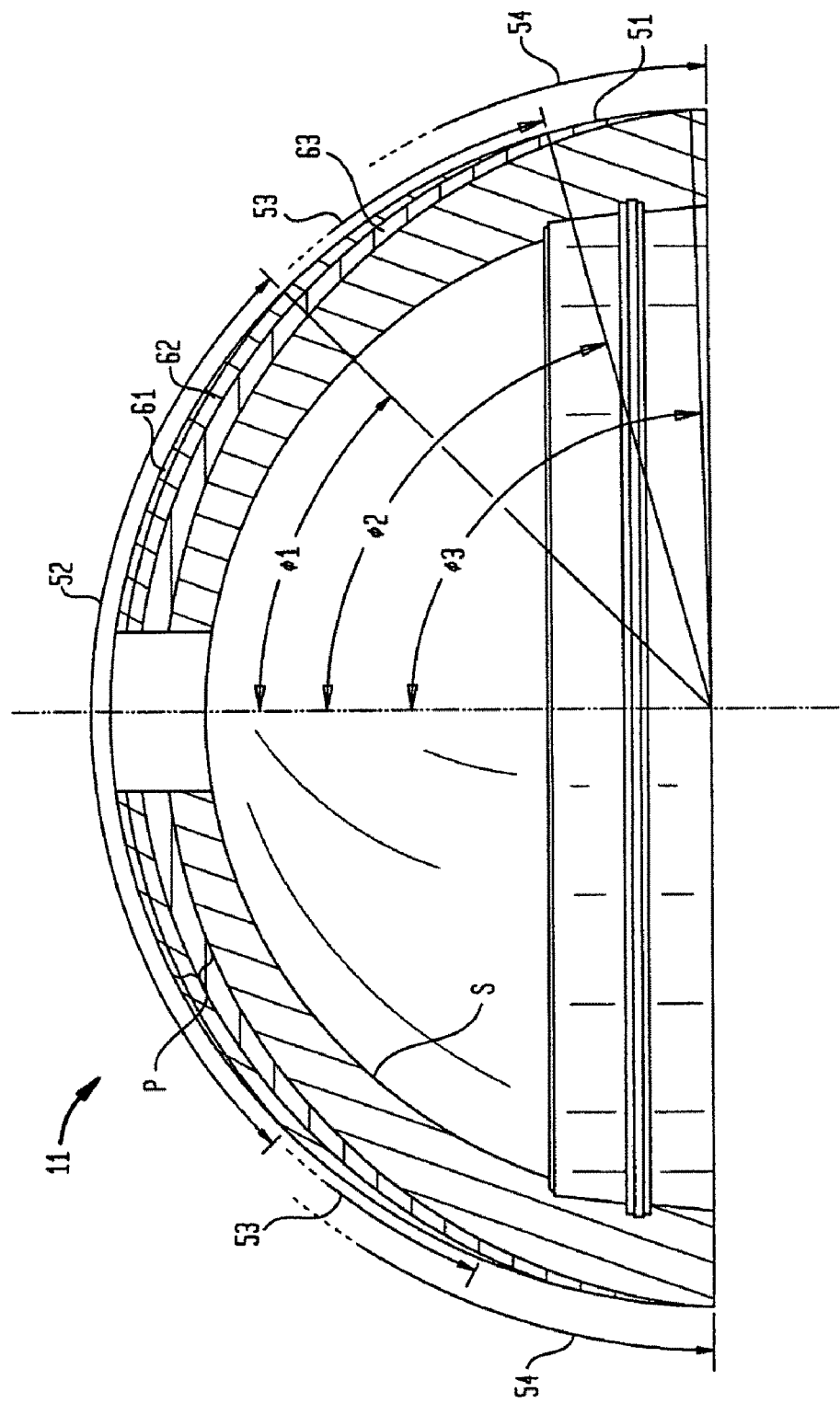
Figure 9:
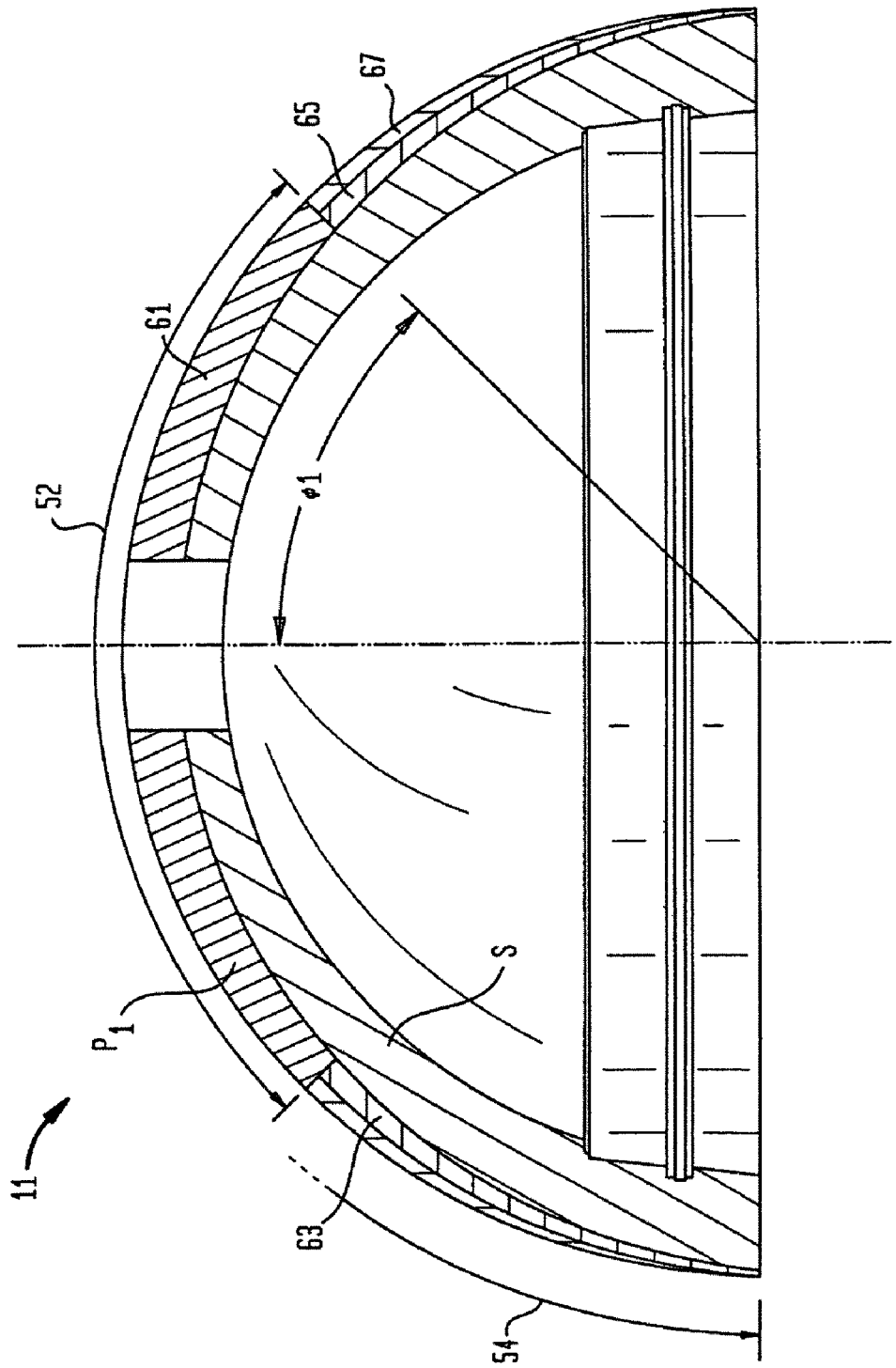
Figure 10:
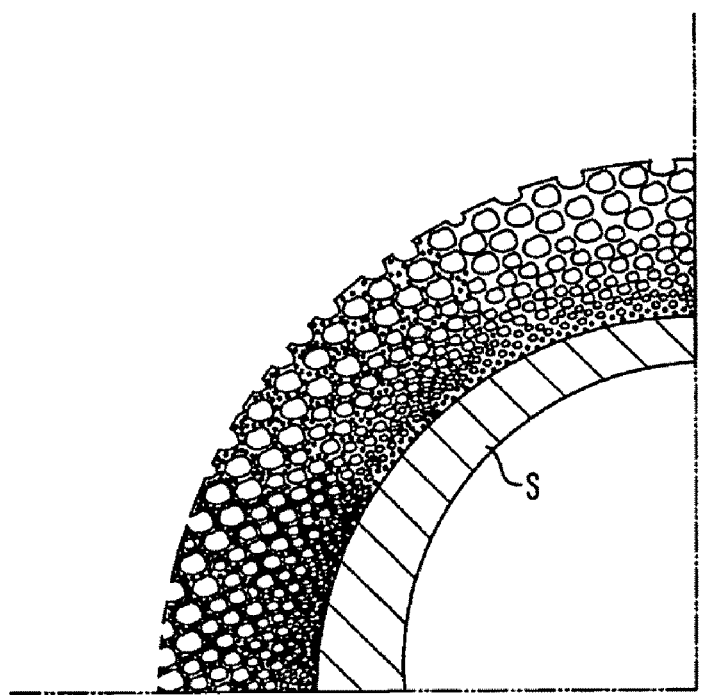
Figure 11:
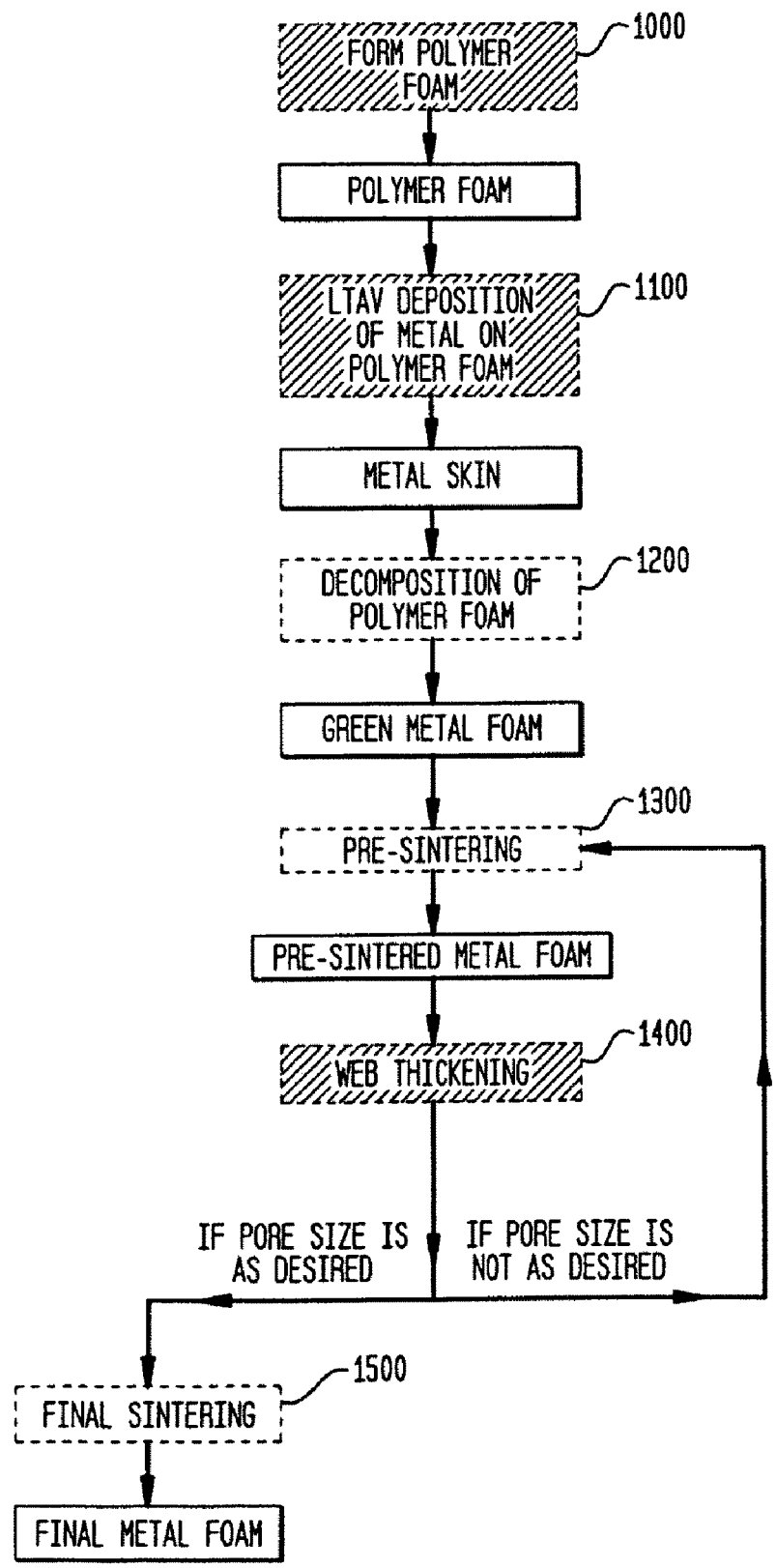
Figure 12:
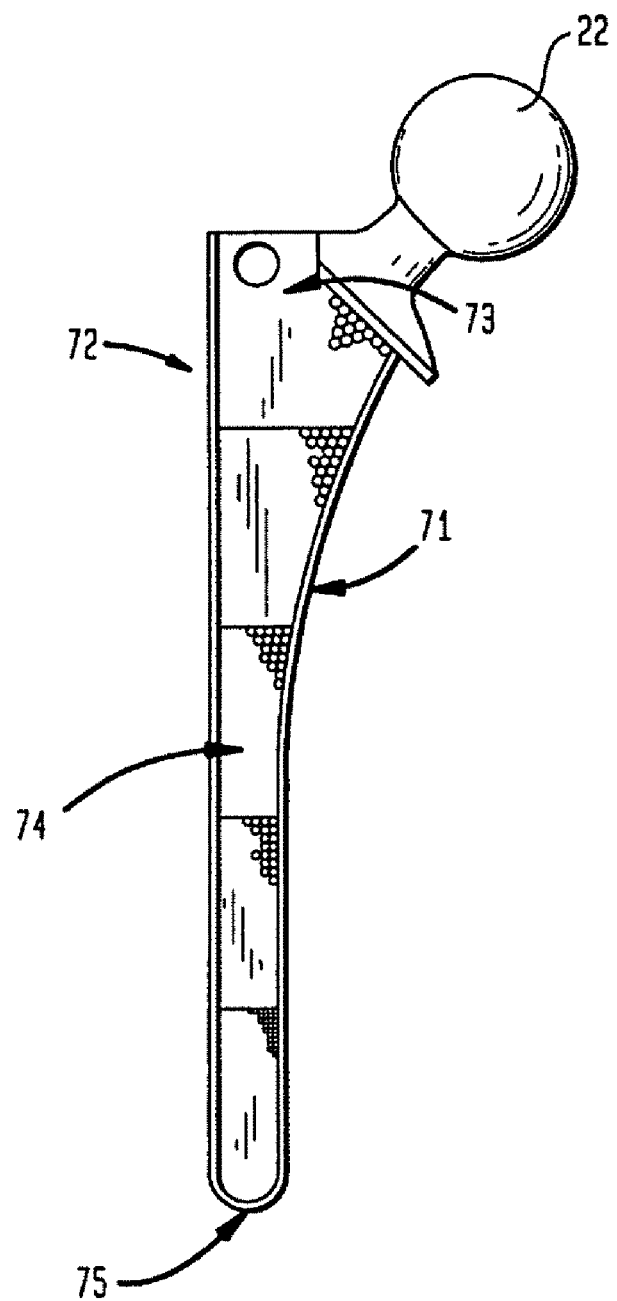

A more accurate appreciation of the subject matter of the present invention and the various advantages thereof can be realized by reference to the following detailed description, which makes reference to the accompanying drawings in which:

FIG. 4 illustrates an embodiment of the invention, a front cross-sectional view of an acetabular cup implant incorporating a porous metal foam structure;

FIG. 5 shows a plan view of the rim and inner surface of the acetabular cup of FIG. 4;

FIG. 6 shows an enlarged cross-sectional view through the polar region of the acetabular cup of FIG. 4 along the line A-A;

FIG. 7 shows an enlarged cross-sectional view through the equatorial region of the acetabular cup of FIG. 4 along the line B-B;

FIG. 8 shows an acetabular cup embodiment of the invention with differing zones of porosity characteristics defined by the polar angle;

FIG. 9 shows an acetabular cup embodiment of the invention with a single zone of porosity characteristics in the polar region and two zones of porosity characteristics in the equatorial region;

FIG. 10 shows a cross-section of a portion of an acetabular cup having a gradient of porosity throughout the volume of the porous metal foam coating;

FIG. 11 shows a general functional block diagram of a method for producing porous metal foam structures in accordance with one of the embodiments of the invention; and FIG. 12 shows an embodiment of the invention with a femoral stem having a three dimensional gradient porous metal foam coating.

DETAILED DESCRIPTION

In accordance with one embodiment, the invention provides a porous metallic foam or foam-like structure suitable for medical device application, especially for orthopedic implants with gradient pore characteristics. The porous metal foam structure has pores defined by metal struts or webs wherein the porous structure has directionally controlled pore characteristics. The pore characteristics controlled include one or more of the metal foam porosity, pore size, pore shape, pore size distribution and web thickness. The pore characteristics may vary in one or more directions throughout the structure. It will be understood that although, for reasons of clarity, the primary varying pore characteristics discussed will be the porosity and pore size, a person of skill in the art will understand the applicability of the various apparatus and methods disclosed to other pore characteristics.

Preferably the pore characteristics are selectively modified to adapt the porous metal foam structure to differing mechanical and biological properties of regions of the adjacent bone in order to optimize various aspects of the implants performance. The modifications include matching the bone characteristics adjacent the structure, such as the bone porosity, strength and modulus of elasticity.

In another aspect, the invention modifies the thickness of the porous metal foam structure in different regions of the structure in order to optimize various mechanical and biological requirements of the implants performance. These requirements include increasing the thickness of the porous structure adjacent cancellous bone to allow deeper bone ingrowth in the higher growth cancellous bone region and to allow the implant to be less rigid and more resilient in order to better match the cancellous bone characteristics, and if desired, absorb shock from implant loading. Conversely, the thickness of the porous structure is decreased adjacent denser bone in response to the typically higher loads imposed in the denser bone regions, both during installation and use, as a result of the relatively higher strength and modulus of elasticity of the denser bone.

In the preferred variant, the porous foam or foam-like structure of the invention is a high strength, open cell, structure defined by metal webs with pore sizes of the foam regions adjacent bone preferably above 100 μm, more preferably, ranging from about 100 μm to about 1000 μm, more preferably still, ranging from about 300 μm to about 500 μm. The porous foam structure adjacent the bone is also characterized by high pore volume or porosity, ranging from about 30% to about 90%, more preferably, from about 60% to about 80%. The foam structure has a porous surface and is preferably a cancellated structure with high interconnectivity throughout. The porous surface interfaces with a bone if the porous foam structure is used in an orthopedic implant. The porous foam structure is preferably made from biocompatible metals, such as titanium, titanium alloys, cobalt-chrome alloy, stainless steel, tantalum, and niobium. The most preferred metals are titanium and titanium alloys. The preferred titanium alloy is Ti-6Al-4V alloy. The foam structure may be in a form of a block, a structure or structures, a tissue in-growth surface or other desirable form or shape.

The porous structure P may be attached to a substrate S (FIG. 4). Preferably, the substrate S is a solid metallic substrate. The substrate S and the porous foam structure P are preferably integrated with each other. FIG. 4 shows the foam structure P in the form of outer porous layer $P_1$ and inner porous layer $P_2$. $P_1$ and $P_2$ are layers having differing pore characteristics and additional layers $P_n$ having differing pore characteristics may also be incorporated in the porous structure P. It should be understood that the shape of the foam structure P and the substrate S shown in FIG. 4 is purely illustrative, and by no means limiting. The thickness or depth d of the porous layer P may be variable over the surface of the substrate, ranging up to 90% of the implant thickness. The thickness of the solid substrate S may be selected as desired and a distinct substrate may not be present or required. The porosity, interconnectivity and other pore characteristics of the porous layer may be variable throughout the depth d, either in a variable gradient manner or in distinct zones.

Preferably, the porous layer P has a porous surface 51 comprising a bone interface surface which typically has a high degree of porosity, interconnectivity and roughness to encourage bone ingrowth and retention. The porosity, interconnectivity and other pore characteristics of the porous layer may be variable over the bone interface surface 51, either in a variable gradient manner or in distinct zones. The surface pore characteristics may be selected to match the bone characteristics adjacent the structure, such as the bone porosity, strength and modulus of elasticity. Thus, for example, the surface pore size adjacent trabecular bone may be 500 µm, while the surface pore size adjacent denser bone may be 100 µm. The surface pore size and porosity may also be tailored in regions of the surface due to mechanical considerations, such as to emulate natural loading of the bone through the implant or to emulate the natural resiliency of bone removed in preparation for the implant. For example, the porosity adjacent a trabecular bone region may be 80% to promote maximum ingrowth and load transfer and to approximate the natural resilience of the trabecular bone. In certain instances, a very low porosity may be required, for instance in order to limit the degree of bone ingrowth or to limit the ingress of wear particles to the bone/implant interface in proximity to the implant bearing surface. A low porosity may also be required in a region subject to a high mechanical load during installation or use that can compromise the integrity of a highly porous structure.

Figure 1:
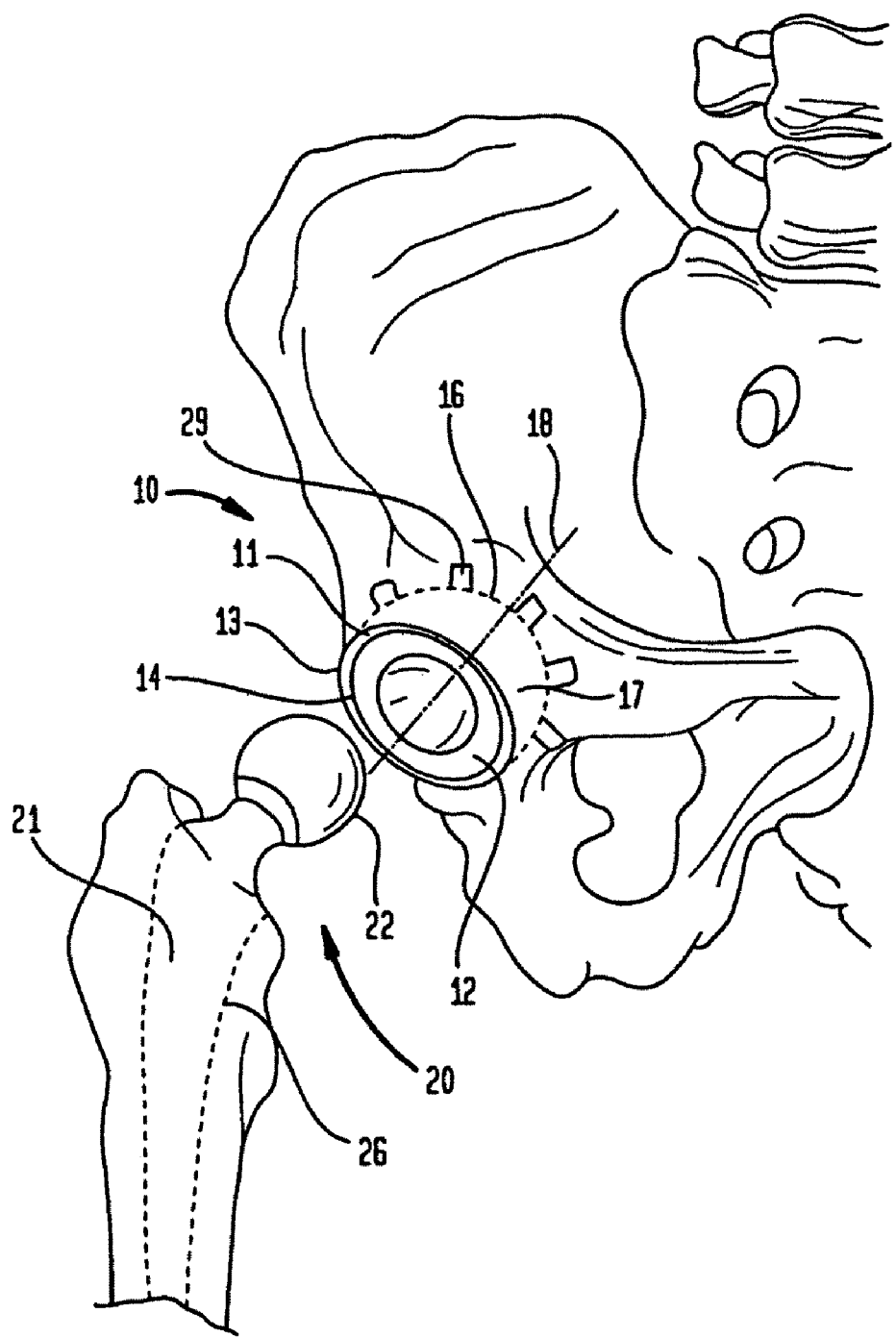
FIG. 1, previously discussed, shows a typical hip joint implant system.
Figure 2:
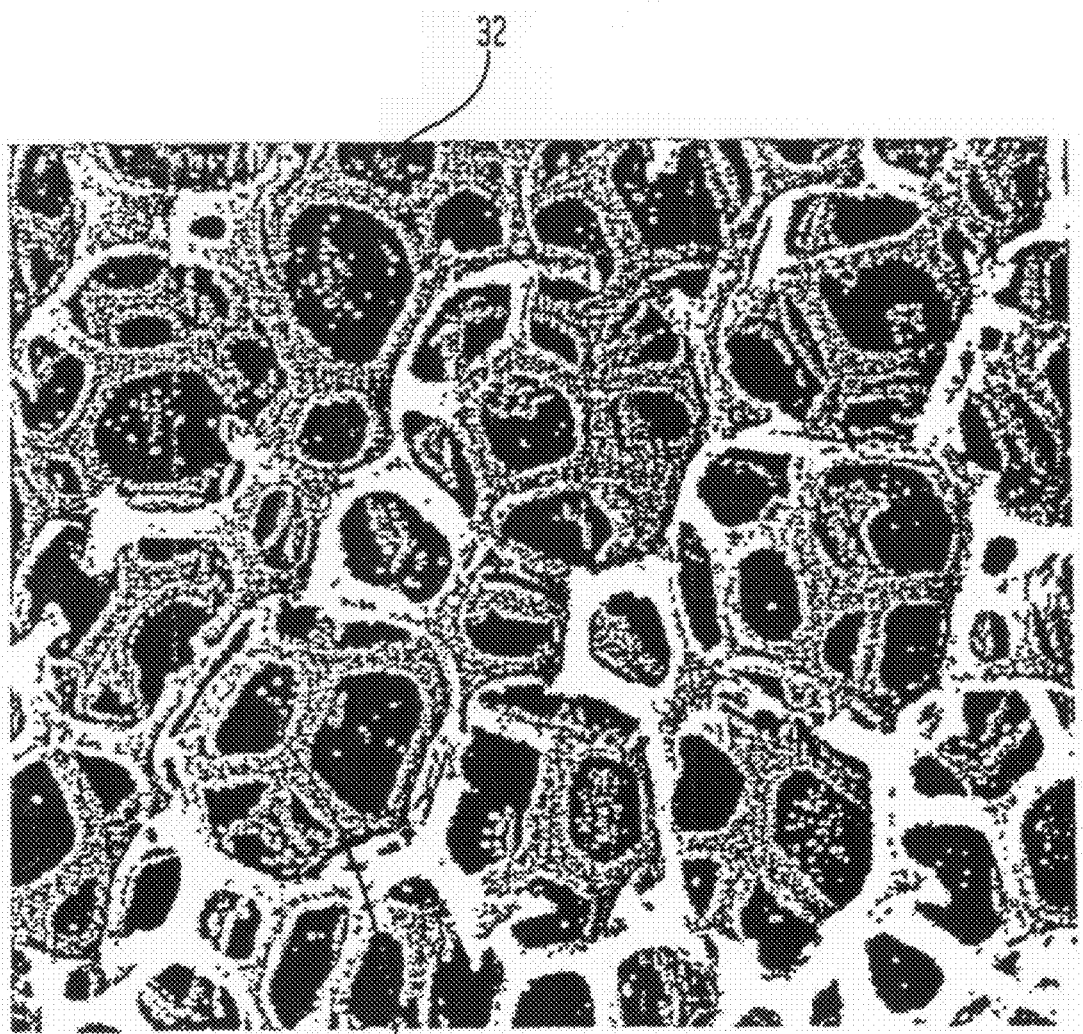
FIG. 2, previously discussed shows scanning electron microscope (SEM) photographs of a titanium-coated cancellated polyurethane foam at 25X.
Figure 3:
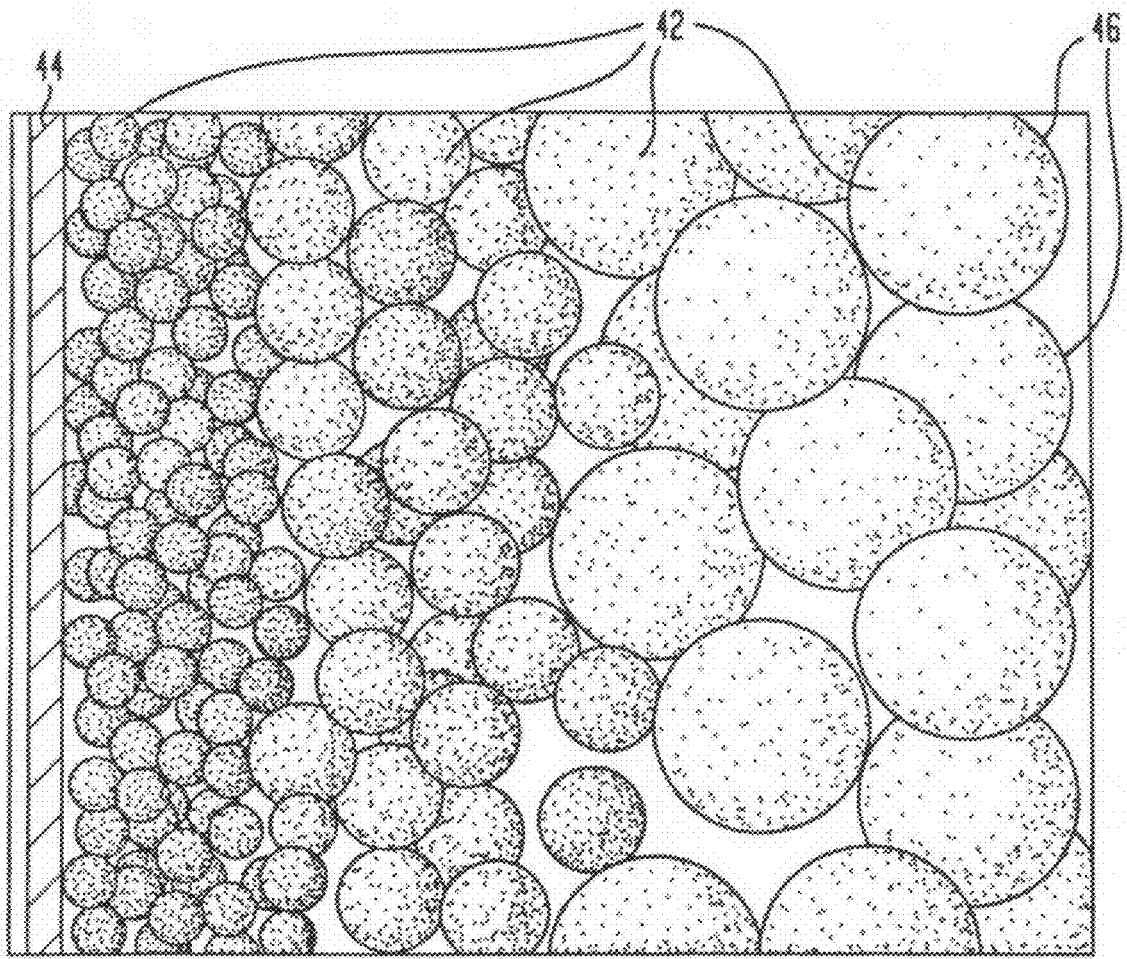
FIG. 3 shows a prior art gradient porous coating.

FIG. 4 illustrates the application of the invention to an acetabular cup shell 11 for an acetabular implant 10 as generally described in FIG. 1. This application may be use either with a socket insert 12 or without an insert in which case the interior surface of the shell 11 acts as the bearing. This embodiment of the invention is intended for a press fit cementless installation in the acetabulum, with bony tissue ingrowth after installation. The porous metal foam structure P is attached to a solid metal substrate S to form the generally hemispherical shell 11 with bone interface surface 51 associated with outer porous layer $P_1$ and substrate interface surface 55 associated with inner porous layer $P_2$ The shell 11 includes a polar region 52 adjacent the pole 18 of the generally hemispherical shell and an equatorial rim region 54 adjacent the rim 17 of the shell. In the instance of an installed acetabular implant, the bone interface surface 51 of the polar region 52 is generally in contact with less dense cancelleous or subchondral bone of the acetabulum while the bone interface surface 51 of the equatorial rim region 54 is generally. in contact with denser subchondral bone.

As illustrated in FIG. 4, the thickness d of the foam structure can be increased, if desired, in the dome region 52 adjacent cancellous bone to allow deeper bone ingrowth in the higher growth cancellous bone region and to allow the implant to be less rigid and more resilient in order to better match the cancellous bone characteristics, and minimize stress shielding. FIG. 6 shows a cross section A-A through the dome region 52 and the relative thickness d of the foam structure. Conversely, the thickness d of the structure is decreased adjacent the denser bone at the equatorial rim region 54 in response to more shallow bone ingrowth potential and typically higher loads imposed in the denser bone regions, both during installation and use, as a result of the relatively higher strength and modulus of elasticity of the denser bone. FIG. 7 shows a cross section B-B through the equatorial rim region 54 and the relative thickness d of the foam structure. Having only a thin thickness d of the foam structure $P_2$ at the equatorial rim is also desirable to limit the area through which any wear debris particles from the implant bearing surfaces can infiltrate the foam structure and come in contact with the bone. FIGS. 7 and 8 also shows that the thickness of the solid substrate S can be increased in the equatorial region to increase the rigidity of the shell and resist distortion of the substrate and bearing surface caused by the relatively high radial loads in the equatorial region created by both the press fit installation of the cup 11 in the acetabular socket and by loading of the implant during use.

The profile of the changing thickness d of the foam structure can be described by various geometrical methods or derived directly from analysis of the desired mechanical properties of the implant using structural static or dynamic analysis methods, such as finite element analysis. The profile of the thickness d may be of constant thickness, or vary linearly with distance along the implant surface or be described by other appropriate mathematical functions. As an example, the acetabular cup depicted in FIG. 4 has a foam thickness d in the dome region of 2.8 mm and the thickness d in rim region is 0.25 mm determined as a sinusoidal function of the respective arcs and centers of the outer surface 51 and the inner surface 55. The difference in thickness d is clearly seen by comparing FIGS. 6 and 7. While depicted in cross section in FIG. 4, the thickness d may also vary in three dimensions, for example, as a function of the angle θ of rotation about the pole 18 as shown in FIG.5.

It is also desirable for the inner surface 55 of the porous metal foam structure to match the characteristics of the substrate of the implant to which the structure is attached, such as the substrate strength and modulus of elasticity. Thus the pore characteristics may vary not only over the surfaces of the porous layer, but through the depth of the porous layer depending on the matching requirements of the particular implant. An outcome of this aspect of the invention is shown in FIGS. 6 and 7, where the respective cross sections through the shell show a small pore size at the inner surface 55 of the porous metal foam structure P and a substantially larger pore size at the bone interface surface 51, the pore size in the dome region 52 depicted in section A-A being larger than the pore size in the equatorial rim region 54 depicted in section B-B. Thus, in this embodiment of the invention, a depth gradient of pore size is established through the foam structure P depending on the boundary conditions and the thickness of P at a given point. Similar depth gradients of other pore characteristics, such as porosity, can be defined based on boundary conditions, such as matching the desired modulus of elasticity; larger scale mechanical conditions, such as achieving a given implant resiliency; or biological conditions, such as controlling the depth and degree of bone ingrowth and fluid infiltration.

Again referring to FIGS. 4, 5, 6 and 7, but considering variation in porosity rather than pore size as described above, an example of various aspects of the invention is an acetabular cup implant with an outer, generally hemispherical, porous metal foam layer for contacting bone P as shown in FIG. 4. The outer layer surface 51 has a first porosity gradient in the equatorial or rim region 54 and a first surface porosity in the equatorial or rim region 54 that is typically in contact with denser subchondral bone of the acetabulum. For particular example, the first surface porosity may be 35% and the first porosity gradient may result in a porosity of approximately 5% in the foam at the inner surface 55. The outer surface layer 51 also has a second porosity gradient in the polar or dome region 52 and a second surface porosity in the polar or dome region 52 that is generally in contact with the cancellous or less dense subchondral bone of the acetabulum. For particular example, the second surface porosity may be 70% and the second porosity gradient may be a linear gradient of 30%/mm having a depth d of approximately 2 mm through the cross-section A-A depicted in FIG. 6. This results in a porosity of approximately 10% in the foam at the inner surface 55. The second surface porosity is greater than the first surface porosity to better allow cancellous bone ingrowth and to allow the dome to be less rigid and more resilient in order to better match the cancellous bone characteristics. The porosity in each region decreases with depth from each respective surface porosity to a lower porosity that better matches the strength and modulus of elasticity of the shell substrate. While the surface porosity has been described as constant in each region, it may also vary as a function of the angle θ of rotation about the pole 18 as shown in FIG. 5. Also the porosity of the foam immediately adjacent the rim 17 may be very low throughout its thickness d in order to better seal the bone interface surface from sinuvial fluids and reduce the potential for the ingress of wear particles from the bearing to the bone interface surface.

It will be understood by a person of skill in the art that while first and second regions 52 and 54, first and second porosity gradients and first and second surface porosities have been described, these zones, porosity gradients and surface porosities may be adjusted and varied to provide gradients of porosity in three dimensions throughout the volume of the generally hemispherical, porous metal foam layer P and that additional discrete intermediate zones, porosity gradients and surface porosities may also be defined, adjusted and varied to transition between the first and second regions, first and second porosity gradients and first and second surface porosities described above to provide varying porosities and porosity gradients in different regions throughout the volume of the generally hemispherical porous metal foam layer. Similarly, it will be understood that these zone and gradient concepts may be applied to other pore characteristics of the porous metal foam layer P as well.

FIG. 8 depicts an acetabular cup with an implementation of such discrete zones having different pore characteristics and, if desired, different pore characteristic gradients. The porous outer layer P consists of a polar partial spherical zone 61, an intermediate partial spherical zone 62 and an equatorial partial spherical zone 63. The polar partial spherical zone 61 overlies the intermediate partial spherical zone 62 and the equatorial partial spherical zone 63 respectively in a polar region defined 52 by a polar angle $\phi 1$. The intermediate partial spherical zone 62 overlies the equatorial partial spherical zone in a region defined by polar angle $\phi 2$, and the outer surface of equatorial partial spherical zone 63 is the bone interface surface 51 in a region defined by polar angles $\phi 2$ and $\phi 3$.

FIG. 9 depicts an acetabular cup with another implementation of such discrete zones having different pore characteristics and, if desired, different pore characteristic gradients. The porous outer layer P consists of a polar partial spherical zone 61 and an equatorial partial spherical zone 63. The polar partial spherical zone 61 overlies the substrate S in a polar region defined 52 by a polar angle $\phi 1$. The equatorial spherical zone 63 is comprised of an inner layer 65 and an outer layer 67. The polar partial spherical zone 61 and the equatorial partial spherical zone inner layer 65 and outer layer 67 each having different pore characteristics. As a typical example using porosity, the inner layer 65 is the least porous, followed by the outer layer 67 and the polar partial spherical zone 61 respectively. If desired, these relative pore characteristic relationships can be altered.

Preferably, the substrate S and the porous layer P are produced from the same metal or alloys of the same metal. The substrate S and the porous layer P may be attached by sintering or other biocompatible attachment processes. The preferred metals for the substrate are biocompatible metals, such as titanium, titanium alloys, cobalt-chrome alloy, stainless steel, tantalum, and niobium. The most preferred metals are titanium and titanium alloys. The preferred titanium alloy is Ti-6Al-4V alloy. The substrate may also be provided with a surface hardening treatment or be coated with a bearing material such as a ceramic. In some instances, the substrate may be integral with the porous metal structure or not be present.

The advantages of the orthopedic implants having the gradient porous foam structure P are related to the method of forming the foam structure. In another embodiment, the invention provides a process for forming gradient porous foam structures of medical devices, especially orthopedic implants and particularly gradient porous foam structures with gradients in more than one dimension.

As previously discussed, the invention provides a method of forming a gradient porous metal foam structure for use in an implantable medical device based on the methods described in U.S. patent application Ser. No. 10/071,667. The methods of the '981 application are extended in the present invention to the fabrication of gradient porous foam structures for implants by new methods that provide varying porosities and porosity gradients in different regions throughout the volume of the porous metal foam layer of the implant.

FIG. 11 shows a general scheme of the process of the '667 application as modified to create gradient pore characteristics. Each of the process steps 1000, 1100 and 1400 which can be modified to create gradient pore characteristics are marked with crosshatching, indicating the option of creating gradient pore characteristics in the gradient porous metal foam structure at that step.

Starting with the unmodified process described in the '667 application, a pyrolyzable polymer foam preform with predetermined pore characteristics is created (Step 1000). The preform includes a polymer web of struts having an open cell, interconnected structure, preferably a cancellated or cancellated structure. A desired biocompatible metal, such as titanium, is deposited on the pyrolyzable polymer foam by low temperature arc vapor deposition (LTAVD or LTAV deposition) (Step 1100). LTAVD is a physical vapor deposition (PVD) method that utilizes a high current, low voltage electric arc to evaporate electrically conductive metals. The metal is evaporated in high vacuum and is deposited as a thin, highly adherent and dense coating on the desired substrate. The LTAV deposition creates a thin layer (or skin) of the metal on the surfaces of the polymer foam. Therefore, the structure of the deposited metal follows the structure of the polymer web, creating a metal skin over the polymer web. Controlling various parameters of LTAVD process, especially the time of the deposition, controls the thickness of the metal skin.

The polymer preform is a low density, high porosity polymer material. As described above, it serves as a three-dimensional template for the metallic porous structure to be formed. Preferably, the preform is shaped in the same manner as the surface of the desired implant. The preform may be placed around a solid portion of the future implant before deposition takes place. More preferably, however, the LTAV deposition is carried out on an unattached preform. The preferable polymer foams decompose with minimal residual contamination upon heating.

The properties of the polyurethane foam preform (e.g., porosity, density, and thickness) are important since they may be used to affect the properties of the final metallic porous structure. Thus, the thickness of the preform determines the thickness of the porous metal structure. The porosity of the polyurethane foam directly affects the pore size of the green metal foam and limits the maximum possible pore size of the final porous structure. In an illustrative non-limiting example, polyurethane foam with a pore size of 1100 μm may be processed by coating with metal powder to yield final metal foam with a pore size of about 600 μm. Under identical processing conditions, polyurethane foam with a pore size of 1400 μm yields a final metal foam with a pore size of about 900 μm.

After the desired thickness of the metal skin is deposited, the polymer foam preform coated with the metal skin is heated at temperatures above the decomposition temperature of the polymer foam in an inert atmosphere, preferably argon gas (Step 1200). The polymer foam decomposes, leaving behind "green" metal foam, which is essentially the metal skin formed in the LTAV deposition. The term "green" is used to refer to a metal foam that has not yet been strengthened by sintering or other similar techniques.

The next step is pre-sintering of the green metal foam (Step 1300). After pre-sintering, the green foam, which is the weak and thin metal skin, is built up to strengthen the metal foam and to obtain the desired pore characteristics (Step 1400). The build up involves increasing the thickness of the internal surfaces of the pre-sintered foam, which may be termed web or strut thickening. The preferred web thickening method involves applying one or more layers of metallic powder and binding it to the pre-sintered metal foam by powder metallurgy techniques. The web thickening may also be accomplished by LTAV deposition, high temperature PVD or chemical vapor deposition. The web thickening reduces the pore size of the metal foam since the thickness of the internal pore surfaces increases.

A binder is used to provide a temporary bond between the surfaces of the pre-sintered foam and external titanium powder. Preferably, the pre-sintered foam is dipped in the binder. Alternatively, an atomized (ultra fine) binder, preferably in the form of a mist, is delivered to the foam by an ultrasonic atomizing nozzle system. A layer of binder forms on all internal and external surfaces of the pre-sintered foam, unless suitable masking is used to exclude the binder. In the most preferred embodiment, the nozzle employs a high frequency (e.g., 65 KHz) sound wave to atomize the solution of the binder into droplets with an average size of from about 20 μm to about 80 μm, more preferably, from about 30 μm to about 40 μm, and to deliver the droplets to the foam at a velocity of from about 0.6 to about 1.2 fps. Because of the small size of the binder droplets, the binder reaches substantially every surface inside and outside the titanium foam, except for masked areas. Also, the use of the ultrasonically-produced ultra fine binder allows delivery of the foam inside the foam without bridging the pores.

Any binder suitable for orthopedic applications, such as fish glue and the like may be used. The preferred binder is a 2% aqueous solution of methyl cellulose with a viscosity of approximately 25 cps. Methyl cellulose leaves less carbon residue on the titanium foam than fish glue after the binder is decomposed in sintering.

After the binder is sprayed, a powder of titanium particles is sprayed on the foam covered with the binder. It is desired to have the potential to deliver the powder to every surface of the foam. For this reason, the size of the titanium particles is smaller than the pore size of the metal foam so that the particles may reach inside the foam without bridging the pores. The preferred titanium powder has a particle size of from about 20 μm to about 100 μm, more preferably from about 40 μm to about 80 μm. Even finer powder may be required for smaller pore sizes. A powder spray delivery system may be used to increase the particle momentum so that the particles may get into the bottom layer of the pre-sintered foam if a uniform coating of powder with respect to the depth d is desired. As the titanium powder comes in contact with the foam, the binder ties the powder to the surfaces of the foam. After the powder is applied, the excess of the powder is removed by air spraying), and the metal foam is sintered producing thickened metal foam with pores smaller than the pores of the metal foam before web thickening.

If a single web thickening step provides metal foam with desired characteristics, such as strength and pore size, the foam may be subjected to final sintering. If further web thickening is necessary, the foam is again pre-sintered and the web thickening step is repeated. After the last web thickening step, the metal foam having the desired thickness, strength, and pore characteristics undergoes a final sintering step, preferably together with the underlying solid metallic substrate (Step 1500). Material removal processes, such as acid etching, may also be used to achieve the desired final characteristics of the foam.

As previously discussed each of the process steps 1000, 1100 and 1400 can be modified to create gradient pore characteristics.

Considering step 1000, the polymer foam preform is modified to have gradient or zonal pore characteristics corresponding to the desired porosity or other pore characteristics of the finished implant. Such a gradient porosity polymer preform may be created, for example, by the buoyancy of the gases in the liquid polymer foam; centrifuging of the liquid foam prior to setting; selected permanent compression of a constant porosity polymer foam precursor; lamination or joining of polymer foam pieces, or by rapid prototyping techniques.

Using buoyancy or centrifuge techniques is useful to create a polymer foam preform with a gradient of lower density pore characteristics, such as a higher porosity or larger pore size, in regions of the preform. The low density pore characteristics are oriented toward an upper portion of a preform when using a buoyancy method or an outward portion of a preform when using a centrifuge technique. For example, if a greater porosity is desired at the polar region of an acetabular cup, that region of the mold for the perform is placed upward, and the liquid polymer foam is not allowed to harden until sufficient time has passed to allow the lower density and more gaseous portion of the liquid foam to rise to the dome region. Furthermore, even within the dome region, a gradient can be created from top to bottom of the preform to create a corresponding gradient normal to the surface through the depth of the preform that will later correspond to the depth d of the acetabular cup shown in FIG. 4. Centrifuge techniques offer the potential to impart even higher forces than gravity to establish density gradient porosity characteristics in order to allow lower process times or greater gradients. For example, in the example of acetabular cup, if a greater porosity is desired at the polar region of a preform of an acetabular cup embodiment, that region of the mold for the preform is placed outward in the centrifuge.

Selected permanent compression of a constant porosity polymer foam precursor is also useful to form the gradient porosity preform. The precursor is formed with excess depths of foam material in the regions where it is desired to decrease the porosity or pore size. These regions are selectively crushed, collapsing the webs or struts, to the final preform shape. The extent of excess foam and degree of crushing or plastic deformation control the decrease of porosity or pore size. The distribution of excess foam in a given region of the precursor can vary and the areas with the most excess foam will have the lowest porosity and a gradient of porosity in the resulting crushed preform. The gradient of pore characteristics of the preform achieved during crushing can be further manipulated by heating regions of the die used to crush the foam to create a temperature gradient in the foam, to allowing greater plastic yielding in the warmer regions of the polymer. For example, when creating the preform for an acetabular cup, the die forming the inner surface can be heated to create a gradient of lower porosity toward the inner surface of the cup. For further example, if additionally the rim region of the preform is heated, not only will the inner surface be less porous, but also the rim. This allows an acetabular cup created from such a preform to have a low porosity of the inner surface and rim, allowing a better mechanical interface with the substrate and sealing of the rim to shield the acetabular socket bone from bearing wear debris.

Multiple pieces of foam having different pore characteristics can be joined or laminated to create the polymer preform. Binders, such as those previously discussed for the sintering operation may be used. As an example, three pieces of foam with separate distinct pore characteristics can be laminated to form a preform for the porous structure P shown in FIG. 8. Each polymer piece corresponds to each of the zones 61, 62 and 63, and is assembled in a laminated fashion to create the polymer foam preform.

The polymer foam preform can also be created with any desirable pore characteristics by rapid prototyping techniques applicable to polymers such as stereo-lithography.

In determining the relationship of the gradient porosity characteristics of the perform to the gradient porosity characteristics of the finished implant, allowance must be made for the web thickening that occurs in steps 1100 and 1400. In an illustrative non-limiting example, polyurethane foam with a pore size gradient having pore sizes ranging from 1100 µm to 1400 µm may be processed by coating with metal powder to yield final metal foam with a pore size of about 600 µm to 900 µm.

Considering Step 1100, the LTAV deposition process or other physical deposition processes are altered to differentially deposit the metal on the polymer preform to create or enhance gradient pore characteristics. As discussed in U.S. Pat. No. 5,534,314, incorporated herein by reference, physical deposition processes are primarily line of sight transfer of the vapor flux and can have inherent patterns of coating non-uniformity. Objects being coated are often rotated or coated from multiple angles in order to achieve uniform coating. In this aspect of the present invention, the LTAV deposition process is modified to take advantage of the directionality of the vapor flux deposited onto the polymer foam in order to build the metal skin to various thicknesses in different regions of the foam and thereby vary the pore characteristics. Low pressure physical vapor deposition processes tend to produce line of sight coating patterns that build up more heavily on the side of the foam facing the source as opposed to surfaces oblique to the source, facing away from the source or in a "shadow" created by overlying foam. Such shadows may also be artificially created by the use of masks placed between the vapor source and the foam to allow less vapor deposition on selected regions of the implant. For example, the inside of an acetabular cup preform may be oriented toward the vapor source in order to create a greater buildup of metal on the inside surface to decrease the pore size and porosity. For further example, a mask may be place in front of the polar region of the cup to decrease the buildup of metal in the polar region. If desired, the mask may be electrostaticly charged to further alter the buildup of metal in the desired region. It is also possible to use the inherent non-uniformity of the vapor flux deposition pattern to position the preform such as to build the metal skin to various thicknesses in different regions of the foam and thereby vary the pore characteristics.

Considering Step 1400, the process of thickening the green metal foam by applying a solution of a binder onto the green foam, applying a metal powder having a pre-determined particle size, and sintering the foam, described in the '981 application is modified to selectively sinter varying amounts of metal powder to different regions of the green metal foam to vary the pore characteristics, such as porosity. In a gradient porous structure special care must be taken to select appropriate particle sizes. If the particle size of the powder is too large, the particles may not be able to penetrate into the smallest pores of the metal foam.

Variations in the amount of metal powder sintered to the foam can be created by varying the amount and location of binder applied; varying the amount and location of metal powder applied; and by selectively removing or migrating binder or metal powder prior to sintering. As described in the '981 application, the cycle of applying the binder, applying the metal powder and sintering can be repeated. By applying and sintering the metal particles to selected regions during latter cycles, the porosity, for instance, can be reduced in the selected regions.

As an example of applying the metal particles to selected regions during latter cycles of the Step 1400 process, after a uniform layer of metal particles is applied and sintered, only the equatorial region is sprayed with binder. After application of metal powder and sintering, the porosity and pore size in the equatorial rim region is further decreased due to the additional thickening of the struts in the region. These steps of selective binder application, powder application and sintering can be repeated in different or overlapping regions to create gradients of pore characteristics or to further decrease the porosity of selected areas, such as the rim area. In another illustrative non-limiting example, 1100 µm polyurethane foam sprayed with binder and coated over its entirety with one layer of metal powder results in a final pore size of approximately 800 µm for regions not subject to further coating, while selected regions coated after sintering with additional binder and receiving two powder layers produce a 600 µm final pore size. Increasing the number of powder layers to three decreases the final metal pore size to approximately 400 µm in those regions receiving three layers.

In similar manner, gradients and differences in pore characteristics in selected zones can be achieved by selectively applying the metal powder rather than the binder. For example, the powder is directionally sprayed and can be sprayed on both surfaces of the porous structure rather than only one surface. In that instance, more powder builds up on the surfaces facing the spray to create a gradient normal to the surface and a minimum of powder in the center of thicker sections of the implant. Metal particles can also be removed or migrated within the porous foam using directed jets of air or a vacuum to create gradient pore characteristics. For example, the buildup of particles on a surface can be enhanced by an additional step of blowing air through the opposite surface to migrate particles away from that surface and toward the built up surface.

As previously mentioned, the embodiments of the invention also provide for orthopedic implants other than the acetabular cup embodiments generally used as examples in this specification. These other embodiments incorporate the gradient porous foam structure P, which is included in the implant as a porous bone-contacting surface, porous block, porous layer or the like. Non-limiting examples of the implants that may include the foam structure P are a vertebral implant, a femoral hip stem implant, femoral and tibial knee joint components, soft tissue attachments, bone defect fillers, shoulder implants, spacers, and any medical device or implant having a surface contacting a bone. In addition to the porous foam structure P, the implant may include a solid metallic substrate S. Preferably, the solid substrate and the porous foam structure are integrated with each other without cement or any other external binding material. For example, as shown in FIG. 12, a femoral component implant 70 may include a solid stem 71 serving as a substrate for the gradient foam structure 72. The gradient foam structure 72 is a bone-contacting porous surface, block or layer having a proximal region 73, an intermediate region 74 and a distal region 75. As an example of possible pore characteristic variations, the gradient porous foam structure 72 not only has a gradient of surface porosity with the porosity being highest in the proximal region 73 and decreasing toward distal end 75, but also the porosity decreases from the surface of the structure 27 in the direction normal to the structure. This arrangement of the gradient porous structure allows for maximum bone ingrowth in the proximal end 73 for a desired load path to the femur and also for better matching of mechanical properties between the solid stem 71 and the less porous portion of the foam structure 72 in contact with the stem. As another example, it may be desirable to increase the porosity in the intermediate region 74 to create greater ingrowth and loading of the bone in that region.

Unless stated to the contrary, any use of the words such as "including," "containing," "comprising," "having" and the like, means "including without limitation" and shall not be construed to limit any general statement that it follows to the specific or similar items or matters immediately following it. Also, if a range is described in the specification and/or recited in the claims, the description/recitation of the range covers every data points within the range, as well as the beginning and ending points of the range. Each such data point, as well as the range defined thereby, should be considered as separately disclosed and/or claimed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cup comprising:
a bearing surface; and
a shell surrounding said bearing surface, said shell having an outer generally hemispherical surface for contacting bone, said hemispherical surface having a pole and an equator, said shell having an inner solid substrate layer with a porous outer layer said porous outer layer having a first thickness and a first porosity adjacent an equatorial region of said hemispherical surface and a second thickness and a second porosity adjacent a polar region of the hemispherical surface, said second porosity and said second thickness being greater than said first porosity and said first thickness,
wherein the thickness of said porous outer layer decreases substantially continuously on moving from said polar region to said equatorial region.

2. The acetabular cup as set forth in claim 1 wherein said first thickness ranges from 0.1 mm to 1.5 mm.

3. The acetabular cup as set forth in claim 1 wherein said shell has at least one aperture therethrough.

4. The acetabular cup as set forth in claim 1 wherein said shell has at least one aperture partially therethrough, said aperture passing substantially through said inner solid substrate layer and not passing through said porous outer layer.

5. The acetabular cup as set forth in claim 1 wherein the porosity of said outer layer decreases through said layer along a gradient normal to said surface.

6. The acetabular cup as set forth in claim 1 wherein the porosity of said outer layer decreases from said first porosity along a gradient normal to said surface through said first thickness.

7. The acetabular cup as set forth in claim 1 wherein the porosity of said outer layer decreases from said second porosity along a gradient normal to said surface through said second thickness.

8. The acetabular cup as set forth in claim 1 wherein said first porosity is in the range from 0% to 50% and the second porosity is in the range from 20% to 90%.

9. The acetabular cup as set forth in claim 1 wherein said first thickness ranges from 0.1 mm to 1.5 mm and said second thickness ranges from 1 mm to 20 mm.

10. The acetabular cup as set forth in claim 9 wherein said equatorial region has pore sizes of between 5 and 200 μm and said polar region has pores of between 100 and 1000 μm.

11. The acetabular cup as set forth in claim 1 wherein said porosity decreases along said outer shell surface on moving from said polar region to said equatorial region.

12. The acetabular cup as set forth in claim 1 wherein the porosity of said outer layer decreases from said first porosity along a gradient normal to said surface through said first thickness.

13. The acetabular cup as set forth in claim 1 wherein the porosity of said outer layer decreases from said second porosity along a gradient normal to said surface through said second thickness.

14. The acetabular cup as set forth in claim 13 wherein said thickness decreases linearly on moving from said polar region to said equatorial region.

15. The acetabular cup as set forth in claim 1 wherein said shell has an overall thickness and said first thickness is approximately less than 25% of said overall thickness and said second thickness is approximately more than 75% of said overall thickness.

16. The acetabular cup as set forth in claim 1, wherein said shell is made from a metal selected from the group of titanium, titanium alloys, cobalt chrome alloys, stainless steel, niobium and tantalum.

17. An acetabular cup comprising:
a bearing surface; and
a generally hemispherical shaped shell having an inner solid substrate layer and a porous outer bone contacting layer surrounding said bearing surface, said porous outer bone contacting layer having a first porosity adjacent an equatorial region of said shell and a second porosity adjacent a polar region of said shell, said second porosity being greater than said first porosity,
wherein said porous layer is thicker in said polar region than at said equatorial region, and
wherein said pore size decreases continuously along said outer shell surface on moving from said polar region to said equatorial region.

18. The acetabular cup as set forth in claim 17 wherein said porous layer has a larger average pore size at said polar region than at said equatorial region.

19. The acetabular cup as set forth in claim 17 wherein said polar region has a first average pore size and said equatorial region has a second average pore size.

20. The acetabular cup as set forth in claim 17 wherein the pores are interconnected.

21. The acetabular cup as set forth in claim 17 wherein said porosity includes a pore size in the equatorial region in the range from 5 to 200 μm and in the range from 100 to 1000 μm in said polar region.

22. The acetabular cup as set forth in claim 21 wherein the rate of decrease of the pore size is linear.

23. The acetabular cup as set forth in claim 17 wherein said porosity decreases along said outer shell surface on moving from said polar region to said equatorial region.

24. The acetabular cup as set forth in claim 17 wherein said shell has at least one aperture therethrough.

25. The acetabular cup as set forth in claim 24 wherein said at least one aperture is covered by a porous layer.

26. The acetabular cup as set forth in claim 17 wherein the porosity of said outer layer decreases through said layer along a gradient normal to said surface.

27. The acetabular cup as set forth in claim 17 wherein the porosity of said outer layer decreases from said first porosity along a gradient normal to said surface through said first thickness.

28. The acetabular cup as set forth in claim 17 wherein the porosity of said outer layer decreases from said second porosity along a gradient normal to said surface through said second thickness.

29. The acetabular cup as set forth in claim 17 wherein said polar region average pore size is in the range from 300 to 1,000 μm and said equatorial region average pore size is in the range from 5 to 300 μm.

30. The acetabular cup as set forth in claim 17 wherein the combined thickness of said solid substrate layer and said porous layer is substantially the same in both said polar region and said equatorial region.

31. The acetabular cup as set forth in claim 17, wherein said shell is made from a metal selected from the group of titanium, titanium alloys, stainless steel, chrome alloys, niobium and tantalum.

32. An acetabular cup comprising:
a bearing surface; and
a shell surrounding said bearing surface, said shell having an outer generally hemispherical surface for contacting bone, said hemispherical surface having a pole and an equator, said shell having an inner solid substrate layer with a porous outer layer said porous outer layer having a first thickness and a first porosity adjacent an equatorial region of said hemispherical surface and a second thickness and a second porosity adjacent a polar region of the hemispherical surface, said second porosity and said second thickness being greater than said first porosity and said first thickness,
wherein said thickness decreases sinusoidally on moving from said polar region to said equatorial region.

* * * * *